(12) United States Patent
Cherif-Cheikh

(10) Patent No.: US 7,445,612 B2
(45) Date of Patent: Nov. 4, 2008

(54) SAFETY INJECTION DEVICE FOR A LIQUID OR SEMI-SOLID COMPOSITION

(75) Inventor: Roland Cherif-Cheikh, Barcelona (ES)

(73) Assignee: Société de Conseils de Recherches et d'Applications Scientifiques, S.A.S., Paris (FR)

( * ) Notice: Subject to any disclaimer, the term of this patent is extended or adjusted under 35 U.S.C. 154(b) by 0 days.

(21) Appl. No.: 09/832,273

(22) Filed: Apr. 10, 2001

(65) Prior Publication Data

US 2001/0037090 A1 Nov. 1, 2001

Related U.S. Application Data

(63) Continuation-in-part of application No. 09/110,773, filed on Jul. 6, 1998, now Pat. No. 6,213,983, which is a continuation of application No. 08/777,634, filed on Dec. 31, 1996, now Pat. No. 5,776,107.

(51) Int. Cl.
*A61M 5/32* (2006.01)

(52) U.S. Cl. ...................................... 604/198

(58) Field of Classification Search ................ 604/198, 604/199, 158, 192–208, 218, 228, 171, 117, 604/232

See application file for complete search history.

(56) References Cited

U.S. PATENT DOCUMENTS

| | | | | |
|---|---|---|---|---|
| 2,460,039 A * | 1/1949 | Scherer et al. | ............... | 604/203 |
| 3,016,895 A | 1/1962 | Sein | ............. | 128/217 |
| 3,572,335 A | 3/1971 | Robinson | .................... | 128/217 |
| 3,884,230 A | 5/1975 | Wulff | .......................... | 128/221 |
| 4,178,928 A * | 12/1979 | Tischlinger | ................. | 604/139 |
| 4,233,975 A | 11/1980 | Yerman | ...................... | 128/218 |
| 4,359,044 A | 11/1982 | Child | ............................ | 128/1 |
| 4,774,091 A | 9/1988 | Yamahira et al. | ............ | 424/426 |
| 4,820,267 A | 4/1989 | Harman | ........................ | 604/60 |
| 4,846,793 A | 7/1989 | Leonard et al. | ............... | 604/62 |
| 4,846,809 A * | 7/1989 | Sims | .......................... | 604/198 |
| 4,850,968 A | 7/1989 | Romano | ...................... | 604/110 |
| 4,994,028 A | 2/1991 | Leonard et al. | ............... | 604/60 |
| 5,098,389 A | 3/1992 | Cappucci | ..................... | 604/158 |
| 5,120,309 A * | 6/1992 | Watts | ......................... | 604/110 |
| 5,151,088 A * | 9/1992 | Allison et al. | ............... | 604/192 |
| 5,242,416 A * | 9/1993 | Hutson | ....................... | 604/192 |
| 5,250,026 A | 10/1993 | Ehrlich et al. | ................. | 604/60 |
| 5,267,972 A | 12/1993 | Anderson | .................... | 604/192 |
| 5,275,583 A | 1/1994 | Crainich | ...................... | 604/264 |
| 5,279,554 A | 1/1994 | Turley | ......................... | 604/60 |
| 5,284,479 A | 2/1994 | de Jong | ........................ | 604/60 |
| 5,433,711 A | 7/1995 | Balaban et al. | ............. | 604/192 |
| 5,487,733 A | 1/1996 | Caizza et al. | ............... | 604/110 |
| 5,634,906 A * | 6/1997 | Haber et al. | ................. | 604/136 |
| 5,658,259 A | 8/1997 | Pearson et al. | | |
| 5,695,463 A * | 12/1997 | Cherif-Cheikh | .............. | 604/60 |
| 5,776,107 A * | 7/1998 | Cherif-Cheikh | ............. | 604/198 |
| 6,110,147 A * | 8/2000 | Perouse | ....................... | 604/198 |
| 6,221,046 B1 * | 4/2001 | Burroughs et al. | .......... | 604/153 |
| 6,461,333 B1 | 10/2002 | Frezza | ......................... | 604/192 |

FOREIGN PATENT DOCUMENTS

| | | |
|---|---|---|
| EP | 0 292 936 A3 | 5/1988 |
| EP | 0 415 504 A1 | 8/1990 |
| EP | 1 090 652 | 4/2001 |
| EP | 1 090 652 A | 4/2001 |
| FR | 1168371 | 12/1958 |
| FR | 2741268 | 5/1995 |
| FR | 2736553 | 1/1997 |
| NL | 8901124 | 12/1990 |
| WO | WO 95/09022 | 4/1995 |
| WO | 98 29152 A | 7/1998 |
| WO | WO 98/29152 | 7/1998 |
| WO | WO 99/22791 | 5/1999 |
| WO | 00 56383 A | 9/2000 |
| WO | WO 00/56383 | 9/2000 |

* cited by examiner

*Primary Examiner*—Ann Y Lam
(74) *Attorney, Agent, or Firm*—Fish & Richardson PC; Alan F. Feeney

(57) ABSTRACT

The invention features a safety injection device for injecting a liquid or semi-solid composition into a subject.

9 Claims, 20 Drawing Sheets

A

B

SAFETY INJECTION DEVICE FOR A LIQUID OR SEMI-SOLID COMPOSITION

CROSS-REFERENCE TO RELATED APPLICATIONS

This application is a continuation-in-part of U.S. patent application Ser. No. 09/110,773, filed Jul. 6, 1998, which issued as U.S. Pat. No. 6,213,983 on Apr. 10, 2001, which is a continuation of U.S. patent application Ser. No. 08/777,634, filed Dec. 31, 1996, which issued as U.S. Pat. No. 5,776,107 on Jul. 7, 1998, the contents of each of which is incorporated herein in its entirety.

BACKGROUND OF THE INVENTION

The invention relates to a device for the parenteral administration through a needle of liquid or semi-solid drug compositions wherein the needle is protected before and after the injection.

The parenteral introduction of pharmaceutically active compounds is preferred over oral dosage for many indications, e.g. where the drug to be administered would partially or totally degrade in the gastrointestinal tract or where there is need for rapid biological response. The need for extratemporaneous preparation of such parenteral compositions is eliminated, or simplified, by the use of pre-filled administration devices in which the liquid to be injected is pre-loaded into the device (e.g. a pre-loaded syringe). Such pre-loaded devices, however, have a number of drawbacks, including the inability to preserve the asepsis or sterility of the needle, as well as the general danger of using an exposed needle. To eliminate these drawbacks, it is necessary to avoid the direct exposure of the needle with the environment both prior to and following injection.

SUMMARY OF THE INVENTION

The invention features a comparatively inexpensive injection device with a needle for parenteral injection of liquid or semi-solid drug compositions into a subject, e.g. a mammal such as a human, wherein the needle is protected before and after the injection.

In general, the invention features an injection device including a housing, the housing having proximal and distal ends and designed to contain a liquid or semi-solid drug composition; a hollow needle, the needle affixed to the distal end of the housing and extending longitudinally within the housing; a plunger, the plunger arranged to slide within the proximal end of the housing; and a hollow sleeve, the hollow sleeve arranged to cover the needle prior to injection and to retract into the housing during injection; wherein the device is designed such that when the sleeve is pressed against the subject, the sleeve retracts into the housing and the drug composition is delivered through the needle and into the subject.

In one embodiment, the device is further designed such that when the drug composition is forced from the housing, the plunger forces the sleeve out of the housing to cover the needle. In a further embodiment, the housing contains the liquid or semi-solid drug composition.

In another embodiment, the device further comprises a septum plunger, the septum plunger slidably arranged within the housing between the plunger and the distal end of the housing. In a further embodiment, the device is configured such that when the drug composition is forced from the housing, the plunger forces the septum plunger into the sleeve, and the septum plunger forces the sleeve out of the housing to cover the needle. In still a further embodiment, the housing contains the liquid or semi-solid drug composition between the plunger and the septum plunger.

In still another embodiment, the housing contains a liquid and a dry drug composition, where the device is designed to combine the liquid and the dry drug composition prior to injection.

In a further embodiment the device comprises a releasable lock which inhibits the movement of the plunger into the housing. In a still further embodiment the device comprises a removable cap which covers the sleeve. In yet a still further embodiment the proximal end of the housing comprises a flange and/or the plunger comprises a flange.

An optional feature of the device comprises a cartridge or tube, said cartridge or tube comprising a distal end, said distal end closed by a cap, seal or septum; a proximal end, said proximal end closed by a plunger tip slidably arranged within the cartridge or tube; and a reservoir between said cap, seal or septum and said plunger tip.

Optionally said cap, seal or septum may be attached to said distal end with a classical clip means, e.g., using a metal ring. The cap, seal or septum and the plunger tip each is made of a suitable material, i.e., a material compatible with the intended use of the injection device. In a preferred embodiment the cap, seal or septum and the plunger tip each independently is made of a non-rigid solid material such as rubber, polybromobutyl, or the like. In a more preferred embodiment the cap, seal or septum and the plunger tip each is made of the same material.

The cartridge or tube is configured to contain a liquid or semi-solid drug composition within the reservoir and is introduced into the housing of the device, e.g., through the proximal end of the housing. The cartridge or tube is further configured such that it can be moved within the housing, e.g., toward or away from the proximal end of the needle. Said cartridge or tube is optionally of a standard variety.

The injection device is configured such that, after the cartridge or tube is connected to the proximal end of the needle, i.e., after the proximal end of the needle pierces the cap, seal or septum located at the distal end of the cartridge or tube, then when the sleeve is pressed against the subject the sleeve retracts into the housing thereby exposing the distal end of the needle and allowing the distal end of the needle to penetrate the subject. Thereafter, when the plunger tip at the proximal end of the cartridge or tube is urged into the cartridge or tube, i.e., toward the distal end of the cartridge or tube, the drug composition is urged from the cartridge or tube through the needle and into the subject.

According to a particular variant of this invention, the cartridge or tube further comprises a proximal compartment located toward the proximal end of the cartridge or tube and a distal compartment located toward the distal end of the cartridge or tube, wherein the proximal compartment and the distal compartment are separated by a plunger. In this variant said proximal compartment contains a liquid component of a composition and the distal compartment contains a solid component of said composition. In this variant the device is configured such that, in operation, the liquid and solid components are mixed prior to injection.

In one embodiment, the device is further configured such that when the drug composition is forced from the cartridge or tube, the cartridge or tube urges the sleeve out of the housing thereby covering the needle after the injection and, optionally, urging the withdrawal of the needle from the subject. In a further embodiment, the cartridge or tube contains the liquid or semi-solid drug composition.

In another embodiment, the cartridge or tube further comprises a septum cap or seal to close the distal end and a septum plunger to close the proximal end of the tube. Said septum cap or seal is fixed by a clip and said septum plunger is slidably arranged within the cartridge or tube. In a further embodiment, the device is configured such that, when the cartridge or tube is urged sufficiently into the housing the proximal end of the needle passes through the septum cap or seal, and, when the drug composition is urged from the cartridge or tube by the septum plunger, said septum plunger urges the cartridge or tube and the cartridge or tube urges the sleeve out of the housing to cover the needle. In still a further embodiment, the cartridge or tube contains the liquid or semi-solid drug composition between the septum cap or seal and the septum plunger.

In still another embodiment, the cartridge or tube contains a liquid and a dry drug composition, where the device is designed to combine the liquid and the dry drug composition prior to injection.

The device can further include a cartridge or tube locking means to inhibit the movement of the cartridge or tube in the housing, e.g., after the cartridge or tube has been connected to the needle. The proximal end of the housing may have a flange and the plunger may also have a flange.

In still another embodiment of the injection device the housing comprises the reservoir and the hollow needle is affixed to the distal end of the reservoir and extends only longitudinally outside said reservoir. A housing or protection sleeve is configured on the plunger and is arranged to slide around the reservoir. The device is configured such that when the drug composition is urged from the reservoir, the plunger housing covers said reservoir. At the end of the injection the plunger is released from the plunger housing, e.g., by the proximal end of the reservoir, and the plunger slides into said plunger housing thereby allowing the plunger housing to cover the needle.

A further object of the invention is therefore an injection device for injecting liquid or semisolid composition into a subject, the device comprising: a reservoir having a proximal and distal end, said distal end being configured to contain a liquid or semi-solid composition; a hollow needle, said needle affixed to the distal end of the reservoir and extending longitudinally outside said reservoir; a plunger arranged to slide within the proximal end of the reservoir; said plunger arranged to retract after injection into a plunger housing slidably connected to the proximal end of the reservoir and arranged to cover the plunger, the reservoir and the needle after injection; wherein the device is designed such that when the plunger housing is pushed around the reservoir, the plunger is pushed into the reservoir, the composition is pushed from the reservoir through the needle and into the subject.

According to a preferred execution mode of this injection device, said plunger housing is disconnected from said plunger due to a release mechanism into said proximal end of the reservoir. According to another preferred execution mode, the protection sleeve is designed to be locked in an irreversible manner by, e.g., mechanical means once the needle has been protected.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patents, patent applications, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

It is believed that one skilled in the art can, based on the description used herein, utilize the present invention to its fullest extent. The following specific embodiments are, therefore, to be construed as merely illustrative, and not limiting.

Figure 1:
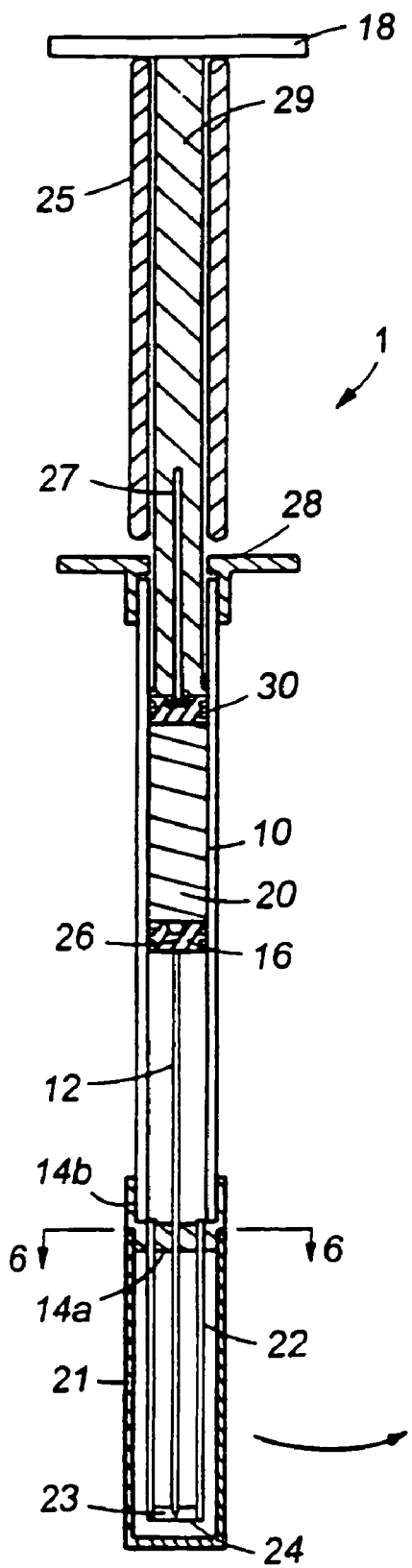
FIG. 1 is a partial cross-sectional view of an injection device prior to use.
Figure 6:
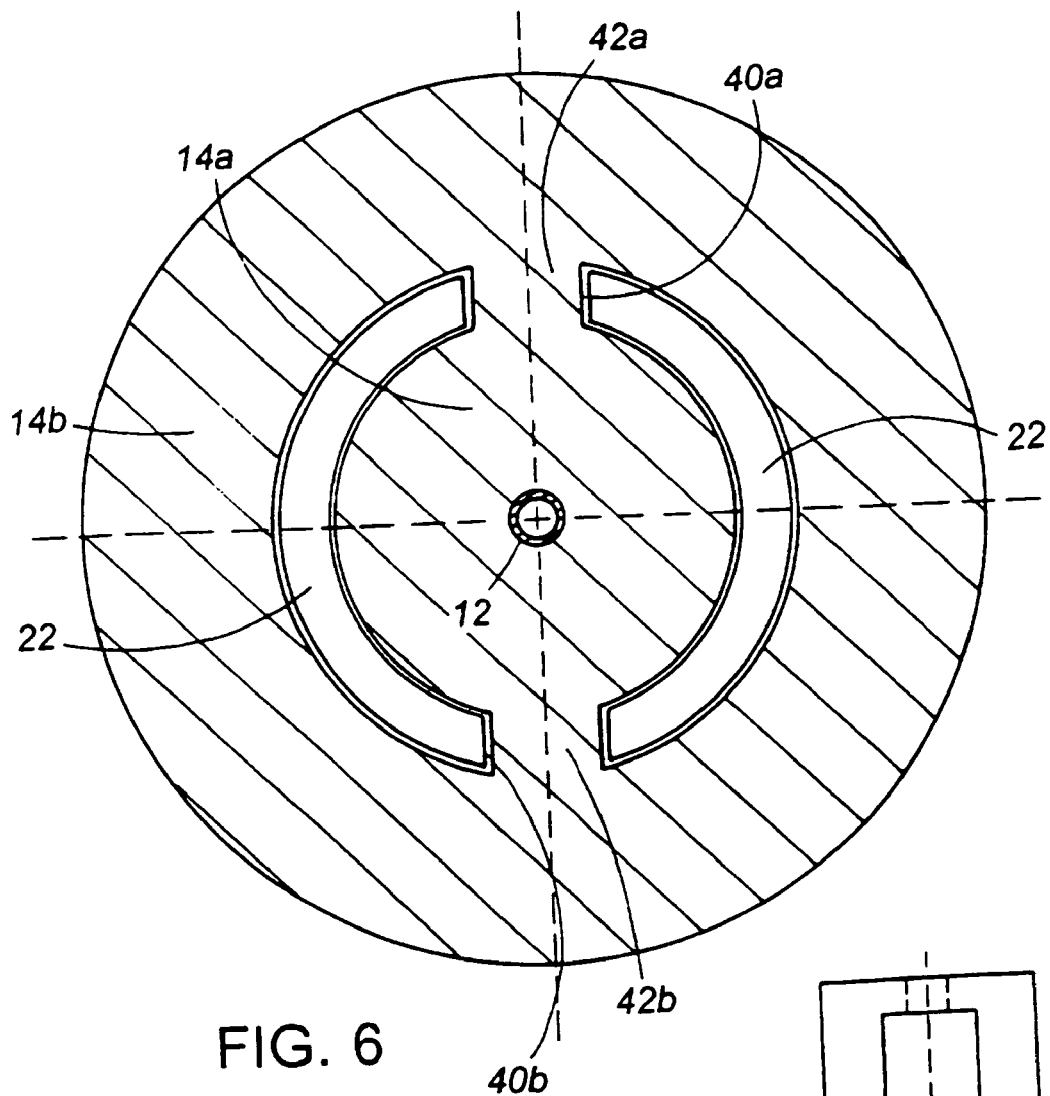
FIG. 6 is a partial cross-sectional view of the injection device through line 6-6 in FIG. 1.

FIG. 1 shows injection device 1 including housing 10, having a proximal end and a distal end 14a, 14b. The distal end of the housing 10 has two holes 40a and 40b partially separating the two parts 14a and 14b of said distal end (as best seen in FIG. 6). Needle 12 is attached to part 14a of the distal end. The housing 10 can be made from a suitably rigid material such as glass, plastic, metal, and the like. The needle 12 is hollow and double-ended, wherein its distal end, remaining outside housing 10, has a point capable of piercing the skin of a subject, and its proximal end, remaining within housing 10, is capable of piercing septum plunger 16. On the proximal end of housing 10 is a flange 28 to assist in removal of device 1 from the subject following injection.

A sleeve 22 surrounds needle 12 so that needle 12 is not fully exposed to the environment until used. Sleeve 22 has longitudinal slots 45a and 45b along its length (see FIG. 7; slot 45b is on the back of the sleeve and is thus not shown). The two parts 14a and 14b of the distal end are joined by radially extending connecting members 42a and 42b (see FIG. 6). Connecting members 42a and 42b, respectively, slide through slots 45a and 45b in sleeve 22, while sleeve 22 slides through holes 40a and 40b in housing 10. Sleeve 22 can be made of suitably rigid material, such as metal, glass, plastic, and the like. Seal 24 covers the opening 23 of sleeve 22 to maintain the sterility of needle 12 and prevent sleeve 22 from unintentionally retracting into housing 10 through holes 40a and 40b prior to injection.

Seal 24 can be made of a thin material, such as plastic or wax, which is easily penetrated by needle 12 during injection. A similar seal can also cover slots 45a and 45b in sleeve 22, to further protect the sterility of needle 12.

Septum plunger 16, contained within housing 10, includes a bore 26, in which needle 12 rests prior to subsequently piercing septum plunger 16. A liquid or semi-solid composition 20 is isolated in housing 10 between the septum plunger 16 and the plunger tip 30, attached to plunger 29. Septum plunger 16 and plunger tip 30 may be made of non-rigid, solid material such as rubber, polybromobutyl, and the like, which allows septum plunger 16 and plunger tip 30 to slide within housing 10 but still maintain sufficient friction with the inner sides of housing 10 to seal composition 20 within housing 10.

The proximal end of plunger 29 has a thumb flange 18 to assist in the depression of plunger 29 into housing 10, and the distal end of plunger 29 has a longitudinal bore 27 to receive needle 12 following injection of composition 20 out and through needle 12. Plunger 29 can be made from a suitably rigid material, such as glass, metal, plastic, and the like. A removable lock 25 may be placed between flange 18 and flange 28 to inhibit further depression of plunger 29 into housing 10 after activation of the device 1, i.e. after the housing 10 is filled with a drug composition and the proximal end of the needle is pierced through septum plunger 16. A removable cap 21 can also be used to protect both needle 12 and sleeve 22 prior to use. Both cap 21 and lock 25 can be made from suitably rigid material such as plastic, metal, rubber, and the like.

Figure 2:
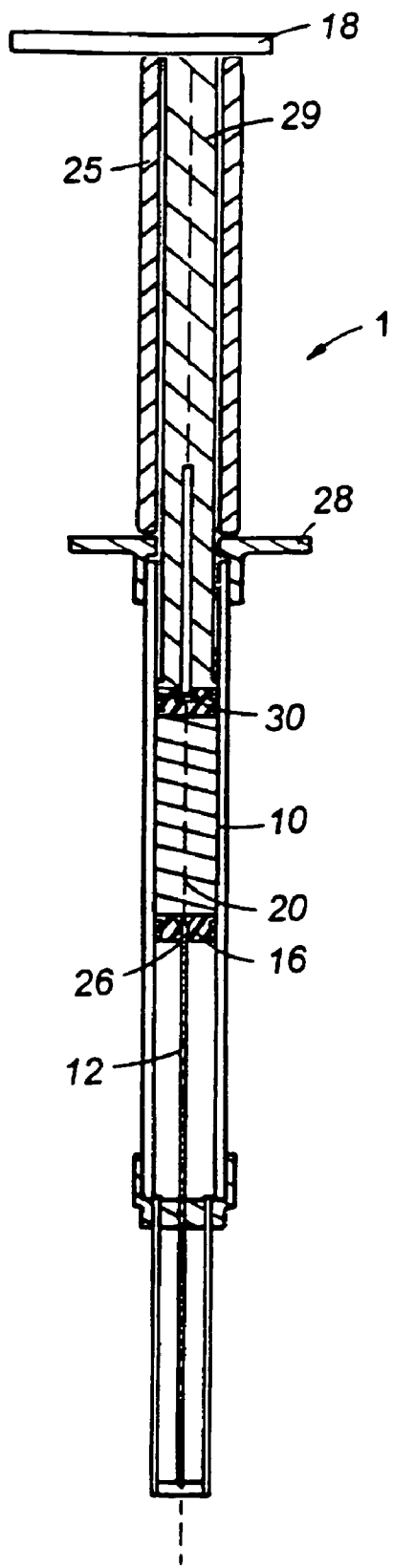
FIG. 2 is a partial cross-sectional view of the injection device of FIG. 1 during use.

FIG. 2 shows device 1 wherein plunger 29 has been pressed into housing 10 to activate device 1 as follows. When plunger 29 is depressed, plunger tip 30, composition 20, and septum plunger 16 are displaced towards the distal end of housing 10. Septum plunger 16 is pierced at bore 26 by needle 12. As a result, the proximal end of needle 12 is exposed to composition 20. Device 1 is now in an activated state. Lock 25, by contacting both flange 18 and flange 28, inhibits the further displacement of composition 20 from housing 10 to needle 12 following activation of device 1, i.e. composition 20 is allowed to fill needle 12, but lock 25 inhibits significant release of composition 20 through needle 12.

Figure 3:
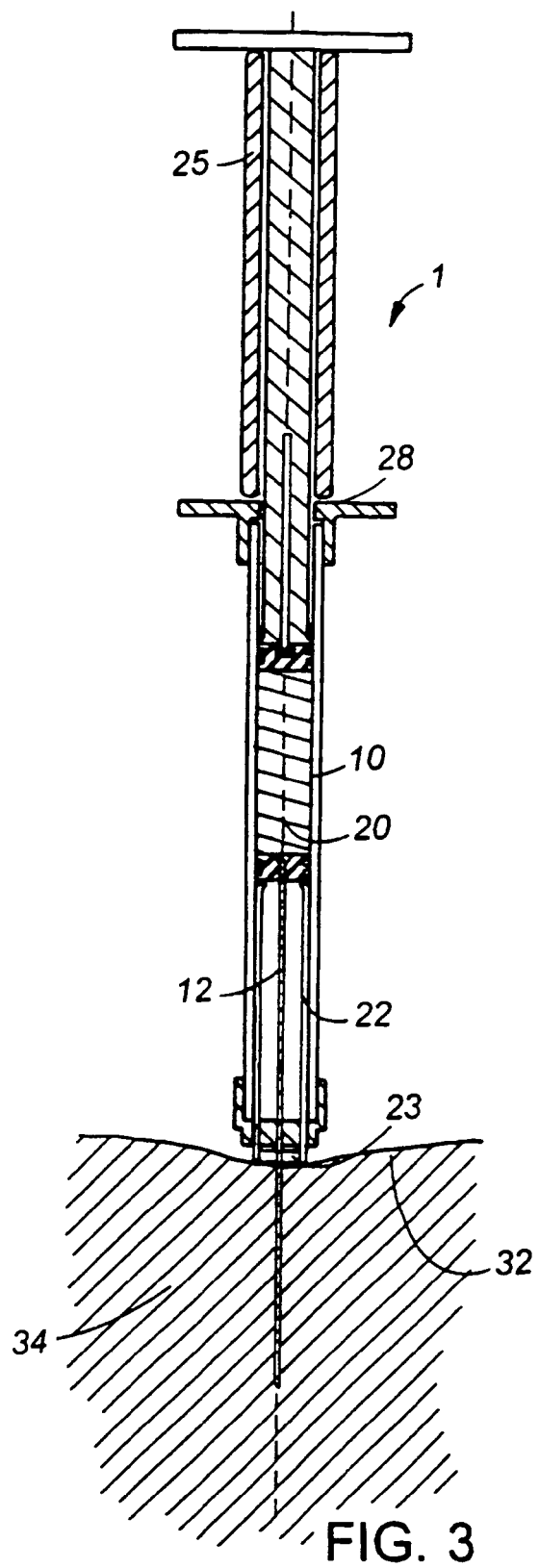
FIG. 3 is a partial cross-sectional view of the device with the needle injected into a subject.

FIG. 3 shows device 1 wherein needle 12 has penetrated skin 32 of the subject being treated. As device 1 is pressed against skin 32, sleeve 22 is retracted into housing 10, through holes 40a and 40b, by the force of pressure against skin 32. Needle 12 passes through sleeve 22 at opening 23. As shown, needle 12 has penetrated through skin 32 into the subcutaneous layer 34.

Figure 4:
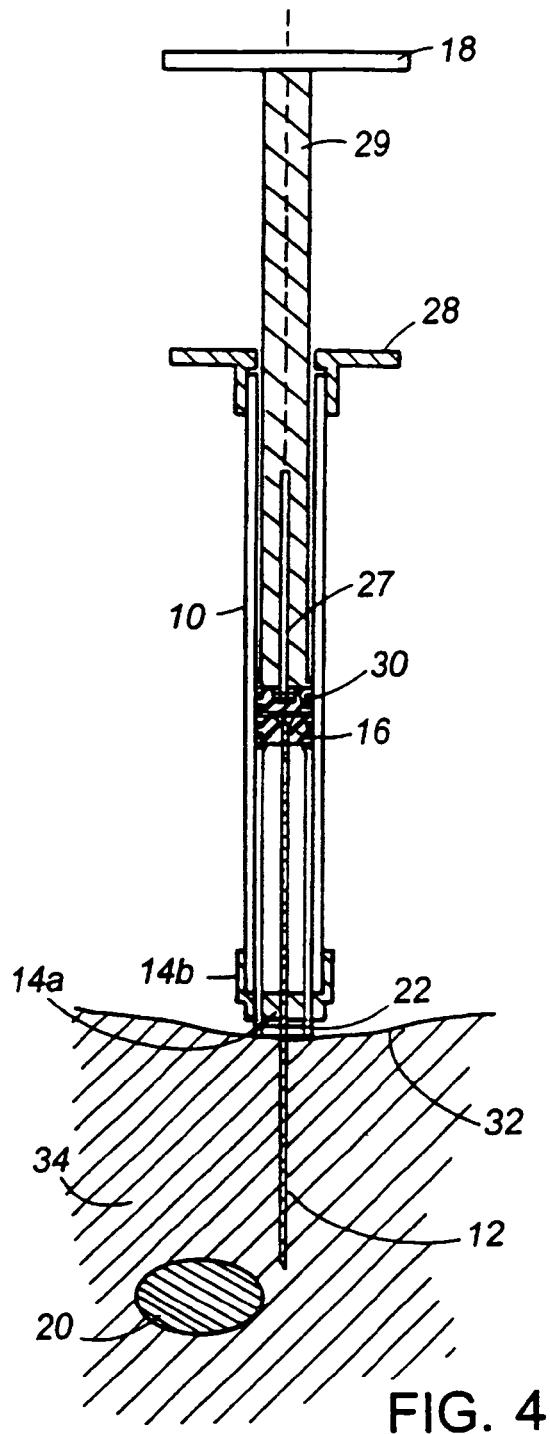
FIG. 4 is a partial cross-sectional view of the injection device being withdrawn from the subject with the drug composition remaining in the subject.

FIG. 4 shows device 1 wherein lock 25 has been removed and plunger 29 has been depressed, which moves plunger tip 30 toward septum plunger 16, thereby injecting composition 20 into subcutaneous layer 34 through needle 12. Once composition 20 has been injected and plunger tip 30 rests against septum plunger 16, housing 10 is moved away from skin 32 by exerting pressure against the lower part of the flange 28 while simultaneously exerting opposing pressure on flange 18 of plunger 29. This relative movement of the plunger 29 and housing 10 causes plunger tip 30 to force septum plunger 16 against sleeve 22 as both plunger tip 30 and septum plunger 16 slide towards parts 14a and 14b of the distal end of housing 10, which in turn forces sleeve 22 out of housing 10 through holes 40a and 40b. As plunger tip 30 and septum plunger 16 are moved toward distal end of housing 10, needle 12 penetrates septum plunger 16, plunger tip 30, and enters bore 27 in plunger 29.

Figure 5:
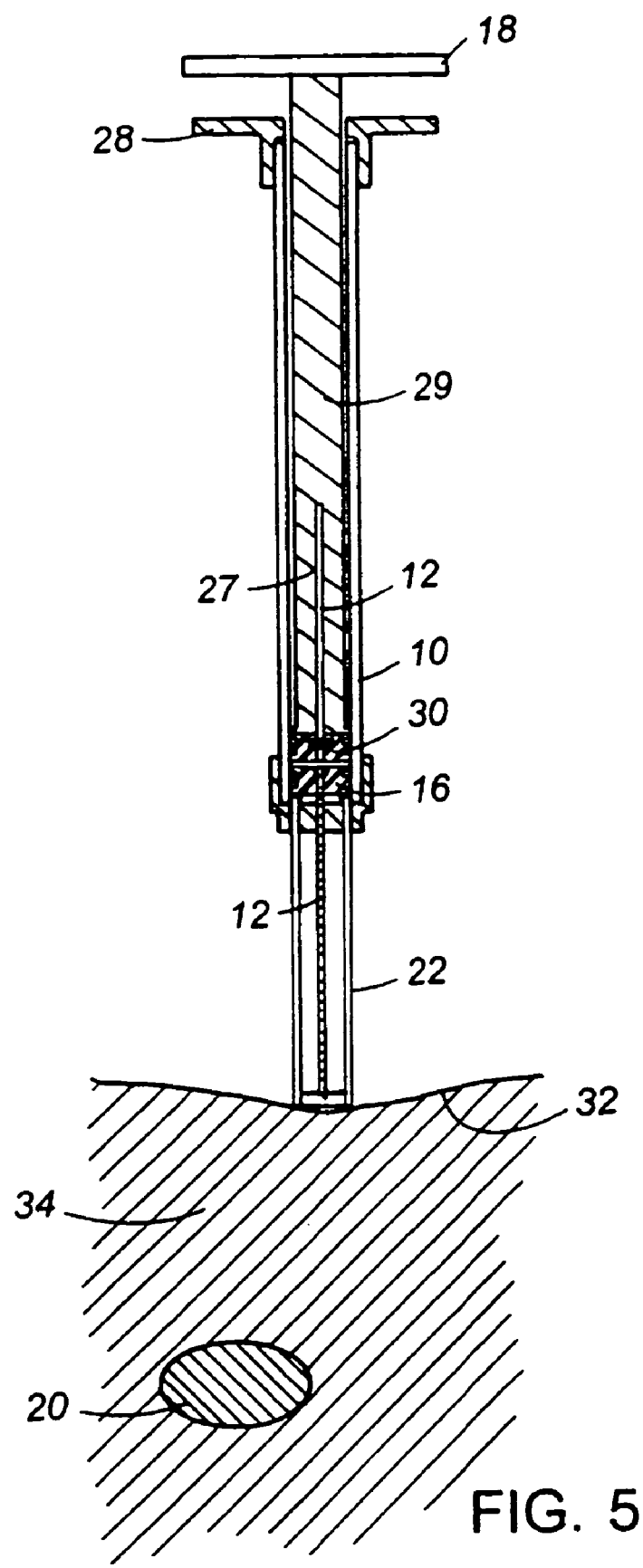
FIG. 5 is a partial cross-sectional view of the injection device following complete withdrawal of the needle from the subject.

FIG. 5 shows needle 12 fully withdrawn from skin 32 and sleeve 22 fully covering needle 12. Composition 20 remains in the subcutaneous layer of the patient. As can also be seen in FIG. 5, the proximal end of needle 12 has been pushed through septum plunger 16 and plunger tip 30 and remains in bore 27 of plunger 29.

FIG. 6 is a cross-sectional view of FIG. 1 at 6-6. FIG. 6 shows holes 40a and 40b in housing 10. Radially extending connecting members 42a and 42b extend through slots 45a and 45b, respectively, to connect parts 14a and 14b of the distal end. Needle 12 is fixed to central part 14a of the distal end, and sleeve 22 can slide through holes 40a and 40b.

Figure 7:
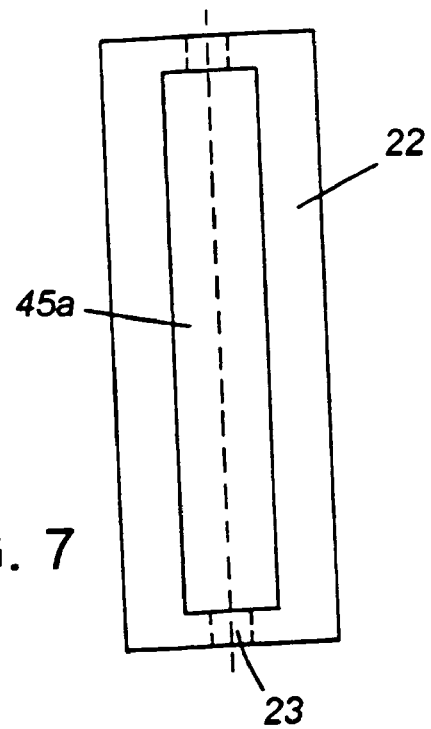
FIG. 7 is a view of the sleeve of the injection device.

FIG. 7 shows an isolated sleeve 22 having slots 45a and 45b (45b is not shown but positioned directly opposite to slot 45a on the other side of sleeve 22) and opening 23. Radially extending connecting members 42a and 42b, respectively, slide through slots 45a and 45b.

Figure 8:
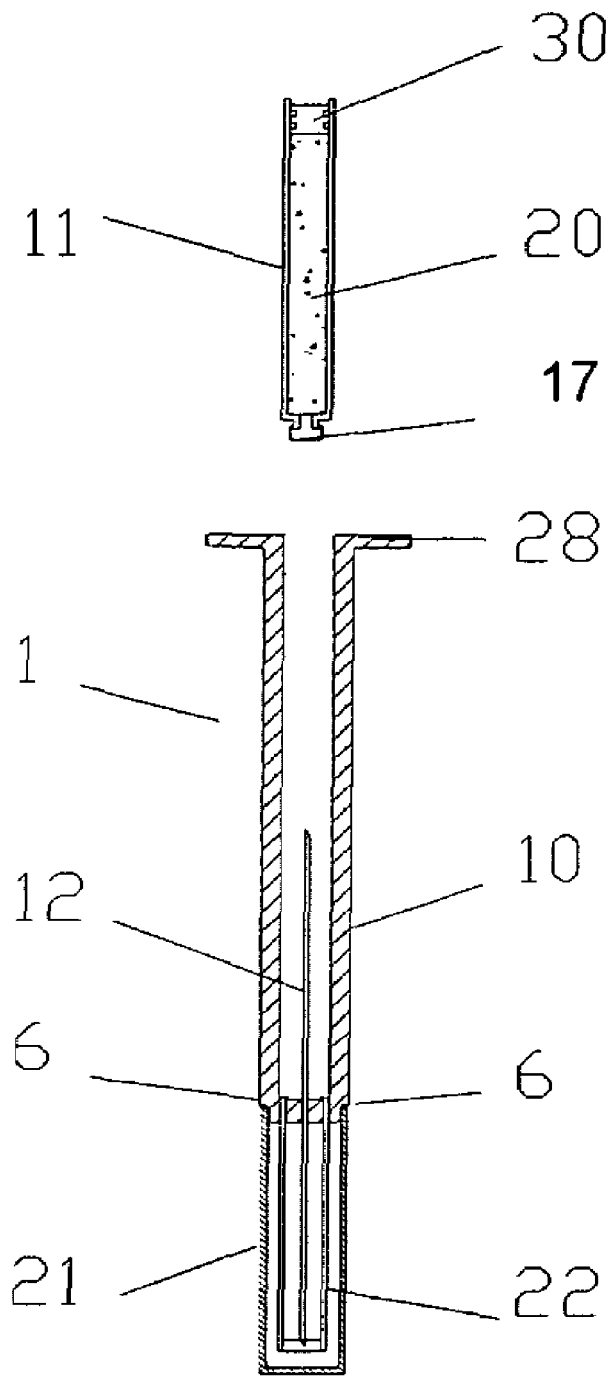
FIG. 8 is a partial cross-sectional view of a cartridge injection device prior to pre-introduction of the cartridge.

FIG. 8 shows a cartridge injection device 1 including a housing 10 having a proximal and a distal end.

Figure 15:
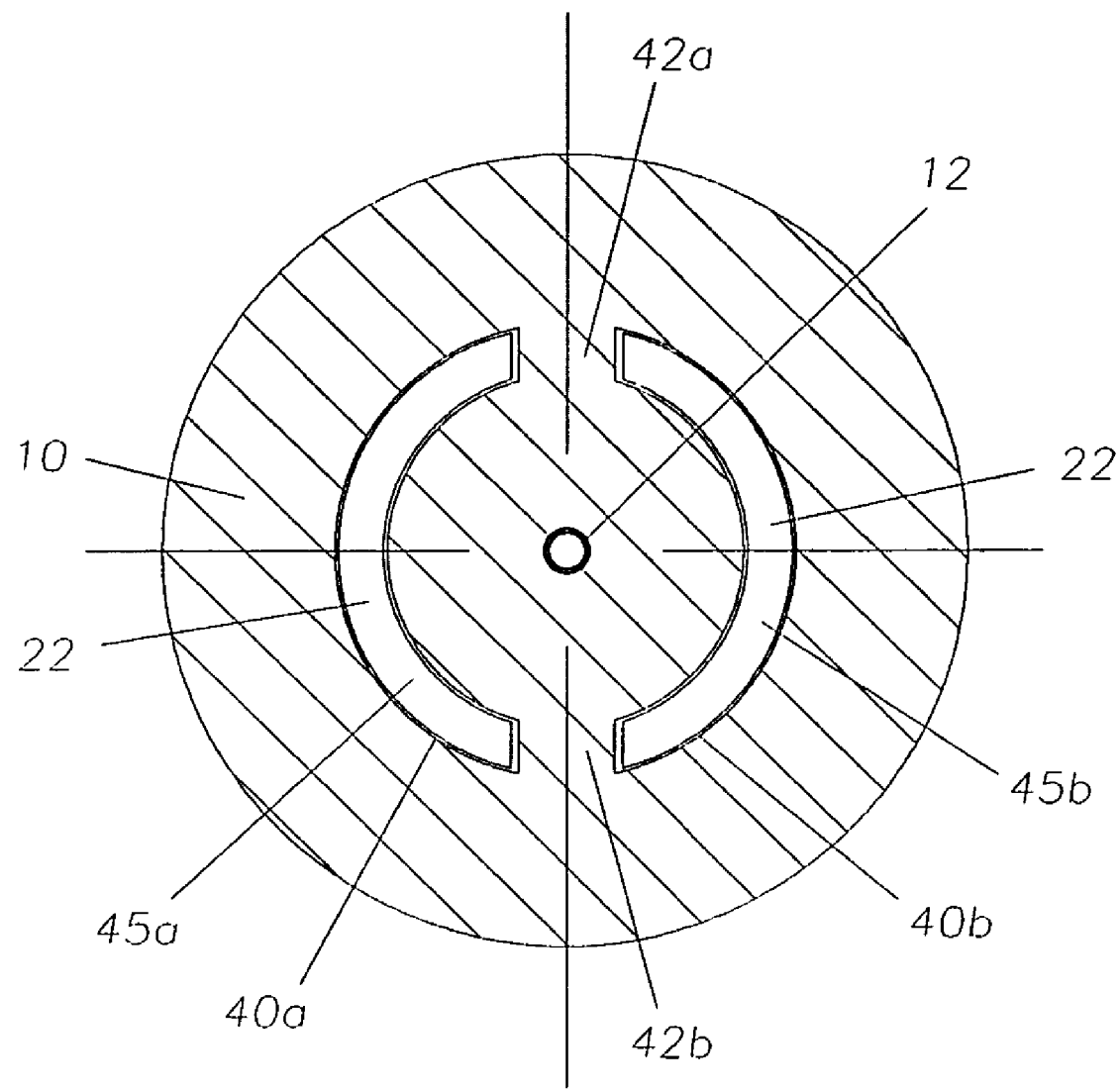
FIG. 15 is a cross-section of the injection device through line 6-6 in FIG. 8.

The distal end of housing 10 has at least one hole and for example two holes, 40a and 40b, partially separating the two parts of the distal end (as best seen in FIG. 15). Needle 12 is attached to the distal end. The housing 10 can be made from a suitably rigid material such as glass, plastic, metal, and the like. The needle 12 is hollow and double-ended, wherein its distal end, remaining outside housing 10, has a point capable of piercing the skin of a subject, and its proximal end remaining within housing 10 is capable of piercing septum cap 17 and septum plunger 30 of the cartridge or tube 11. On the proximal end of housing 10 is a flange 28 to assist in injection. The removal of device 1 from the subject following injection is assisted by extension of sleeve 22.

A sleeve 22 surrounds needle 12 so that needle 12 is not fully exposed to the environment until used. Sleeve 22 has at least one longitudinal slot along its length, and for example two, 45a and 45b (see FIG. 15). The two parts of the distal end are joined by radially extending connecting members 42a and 42b (see FIG. 15). Connecting members 42a and 42b respectively slide through slots 45a and 45b in sleeve 22, while sleeve 22 slides through holes 40a and 40b in housing 10. Sleeve 22 can be made of suitably rigid material such as glass, plastic, metal and the like.

A seal 24 (not shown) on needle 12 can be made of a thin material, such as a plastic sheet, a plastic packaging material or a bag which is easily penetrated by needle 12 during injection. A similar seal can also cover the sleeve 22 to further protect the sterility of the needle 12.

Septum plunger 16, contained within housing 10, can include a bore 26 in which needle 12 rests prior to subsequently piercing septum plunger 16. A liquid or semi-solid composition 20 is isolated in the cartridge 11 between septum plunger 16 and plunger tip 30. Septum plunger 16 and plunger tip 30 may be made of non-rigid solid material such as rubber, polybromobutyl, or the like, which allows plunger tip 30 to slide within cartridge 11 but maintaining sufficient friction with the inner sides of the cartridge 11 to seal composition 20 within cartridge 11.

Figure 11:
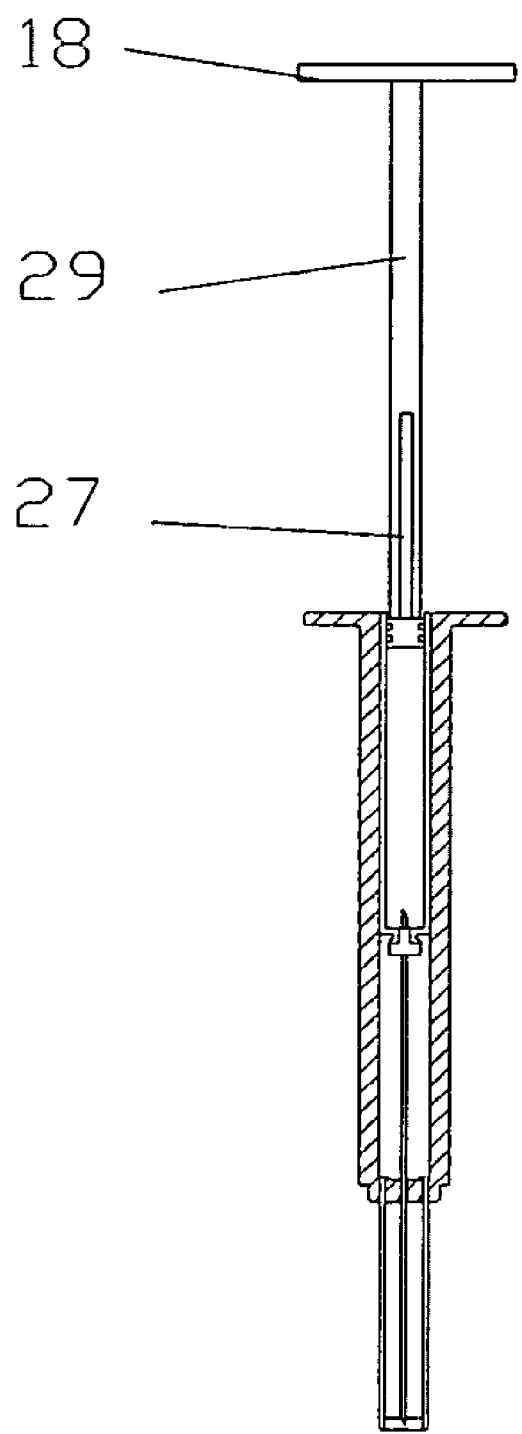
FIG. 11 is a partial cross-sectional view of the cartridge injection device of FIG. 10 during use after plunger setting.

The proximal end of plunger 29 has a thumb flange 18 to assist in the depression of plunger 29 into cartridge 11 and the distal end of plunger 29 has a longitudinal bore 27 to receive needle 12 following injection of composition 20 out and through needle 12 (see FIG. 11). Plunger 29 can be made from a suitably rigid material such as glass, plastic, metal and the like. A removable lock 25 may be placed between flange 18 and flange 28 to inhibit the further depression of plunger 29 into housing 10 after activation of device 1, i.e. after the housing 10 is filled with a tube or a cartridge and the proximal end of the needle is pierced through septum cap 17.

A removable cap 21 can also be used to protect both needle 12 and sleeve 22 prior to use. Both cap 21 and lock 25 can be made from suitably rigid material such as plastic, metal, rubber, and the like Septum cap 17 on distal end of cartridge 11 is sealed, e.g., with a metal ring (not shown). A liquid or semi-solid composition 20 is isolated in cartridge or tube 11 between the septum cap 17 and the plunger tip 30, which will be attached to plunger 29 (see FIG. 11). The cartridge or tube 11 can be connected to the proximal end of needle 12 by applying pressure to the proximal end of the cartridge or tube, e.g., by pushing with the thumb (see FIG. 10).

Septum cap 17 and plunger tip 30 may be made of non-rigid material such as rubber, polybromobutyl, and the like, which allows needle 12 to pierce septum cap 17 and plunger tip 30, and allows plunger tip 30 to slide sealably within cartridge or tube 11.

Figure 9:
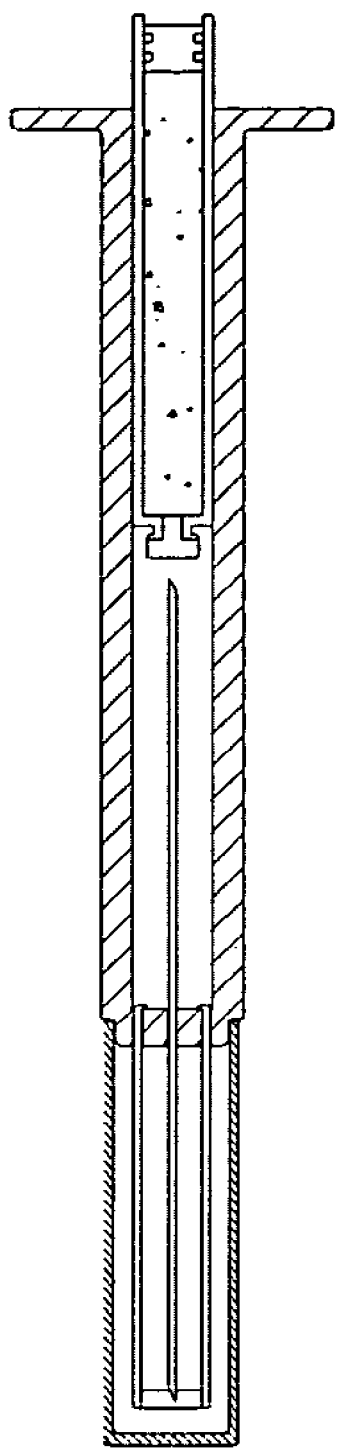
FIG. 9 is a partial cross-sectional view of a cartridge injection device prior to use.

FIG. 9 shows, during use of device 1, the introduction of cartridge or tube 11 into the housing 10.

Figure 10:
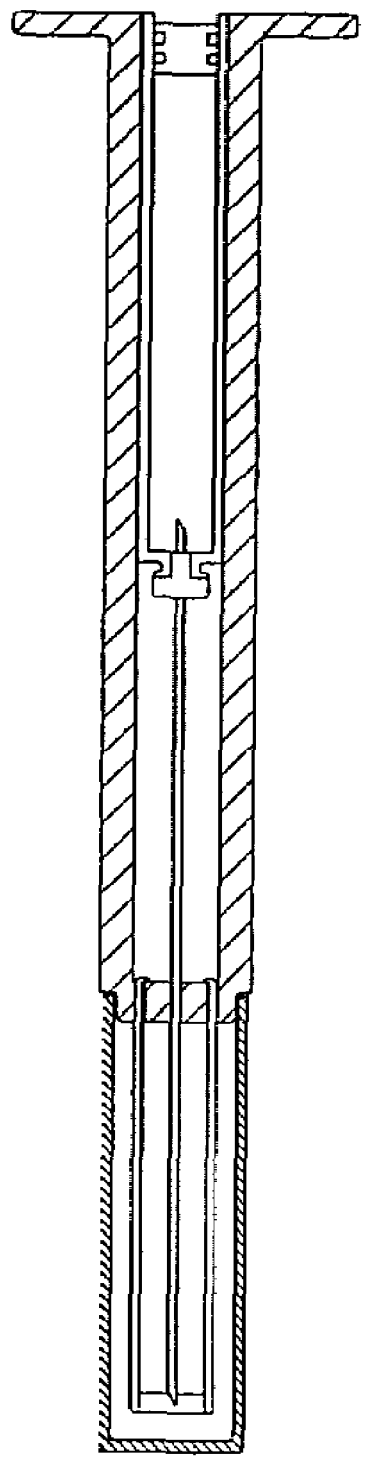
FIG. 10 is a cross-sectional view of the cartridge injection device of FIG. 9 during use after connection of the cartridge to the needle.

FIG. 10 shows the connection of cartridge or tube 11 on needle 12 through septum cap 17.

FIG. 11 shows settlement of plunger 29 on plunger tip 30.

Figure 12:
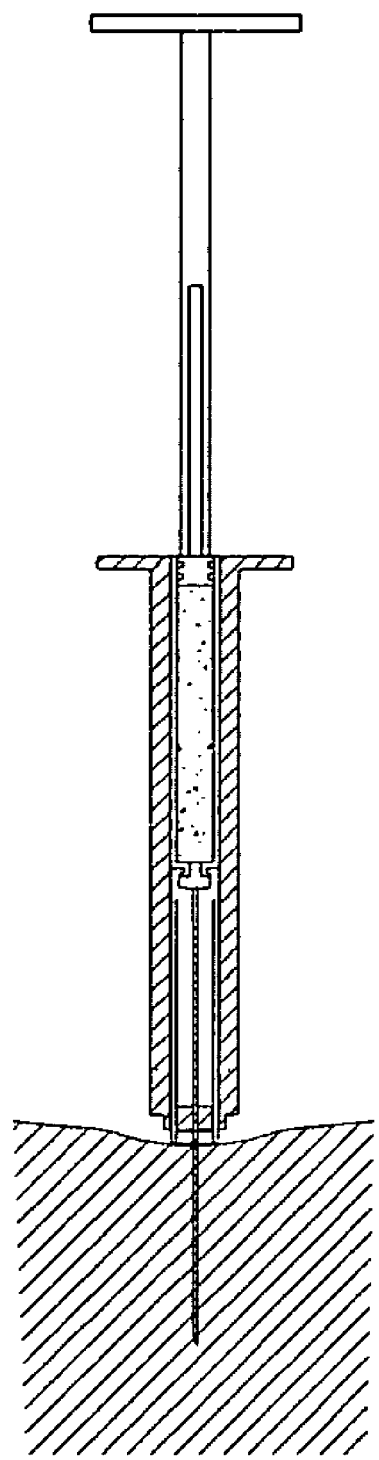
FIG. 12 is a cross-sectional view of the cartridge injection device with the needle injected into a subject.

FIG. 12 shows injection of needle 12 with retraction of sleeve 22 into housing 10.

Figure 13:
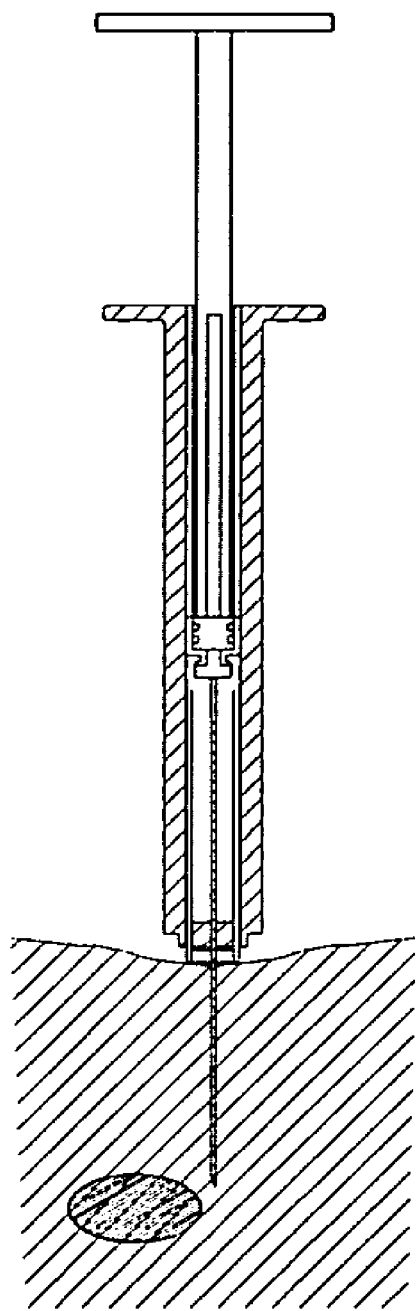
FIG. 13 is a partial cross-sectional view of the cartridge injection device being withdrawn from the subject with a drug composition remaining in the subject.

FIG. 13 shows injection of composition 20 into the tissue, e.g., using thumb on plunger flange 18 and the other fingers on housing flange 28.

Figure 14:
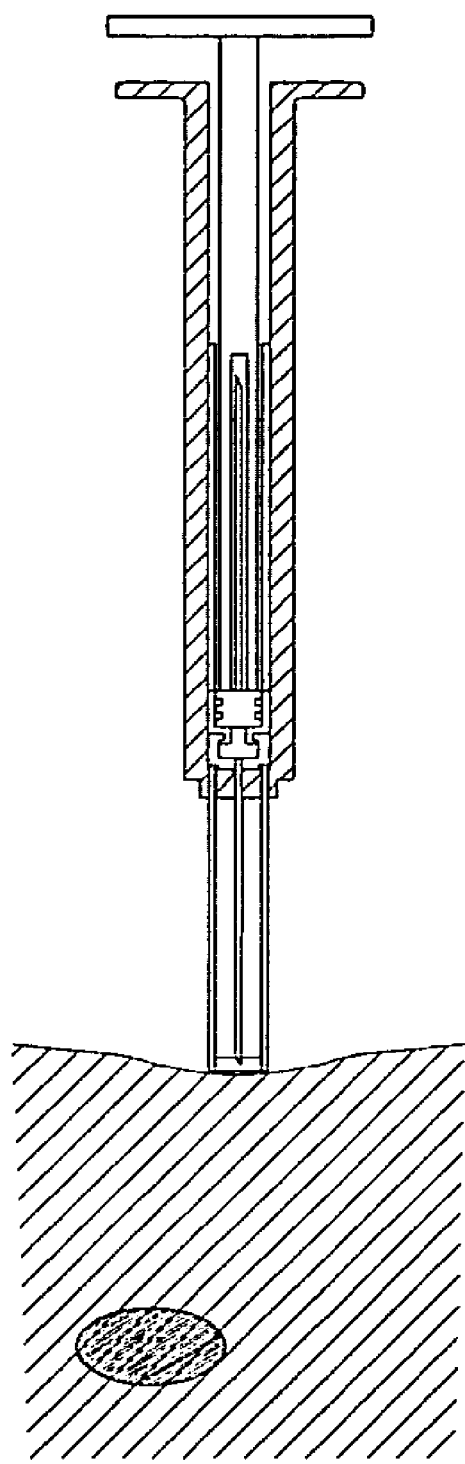
FIG. 14 is a partial cross-sectional view of the cartridge injection device following complete withdrawal of the needle from the subject.

FIG. 14 shows removal of the device from the subject following injection, where cartridge or tube 11 urges sleeve 22 from housing 10 around needle 12 and, consequently, removes needle 12 from body tissue.

FIG. 15 shows a cross-section, through line 6-6 shown in FIG. 8, of distal end 14b of housing 10 with two apertures or holes 40a and 40b through which slots 45a and 45b of sleeve 22 slide. Two connecting members 42a and 42b separate the holes and connect external part of the housing 10 with the internal part where needle 12 is fixed.

Figure 16:
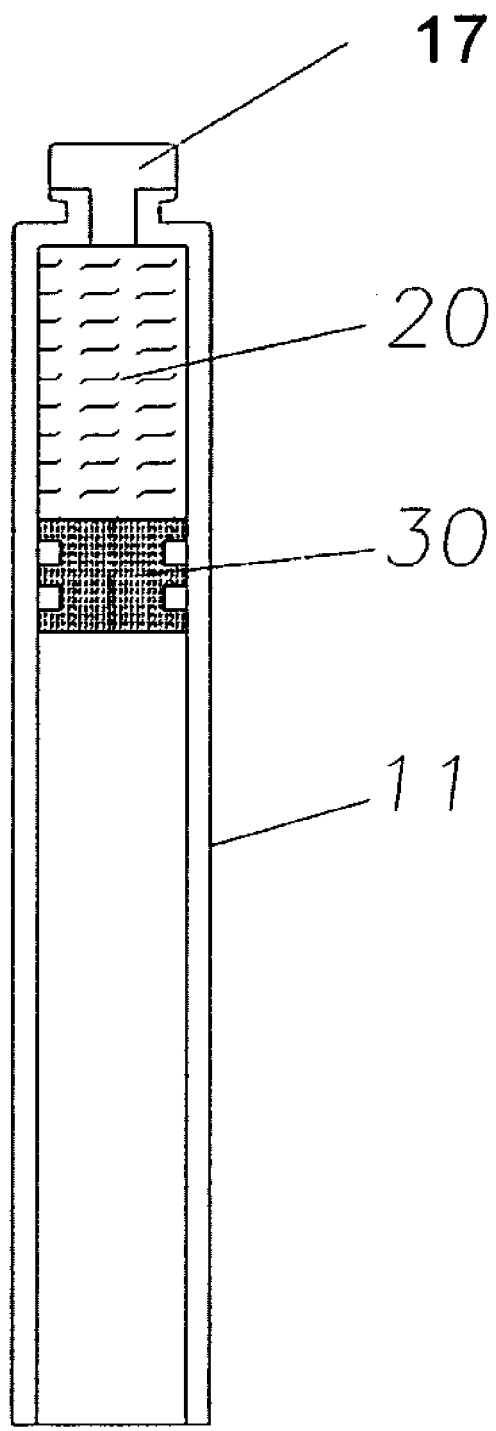
FIG. 16 is a cross-section of a cartridge containing a liquid or semi-solid composition.

FIG. 16 shows a cartridge or tube 11 used in the housing 10 of device 1 with composition 20 between septum cap 17 and plunger tip 30.

FIG. 17A shows a cartridge or tube 11 used in the housing 10 of device 1 with a releasable lock 50. The liquid part of the composition 20B is loaded in cartridge or tube 11 between two septum plunger 30A and septum plunger 30B. Septum plunger 30A is placed into cartridge or tube 11 just before by-pass 51. Septum plunger 30B is locked with the lock 50 in contact with cartridge or tube 11. The solid part of the composition 20A is loaded, e.g., under vacuum, in cartridge or tube 11 between septum plunger 30A and septum cap 17.

FIG. 17B shows cartridge or tube 11 of FIG. 17A after removal of the releasable lock 50. The composition 20 is prepared by passage of the liquid part of the composition 20B through the by-pass 51 into the solid part under vacuum.

Figure 17:
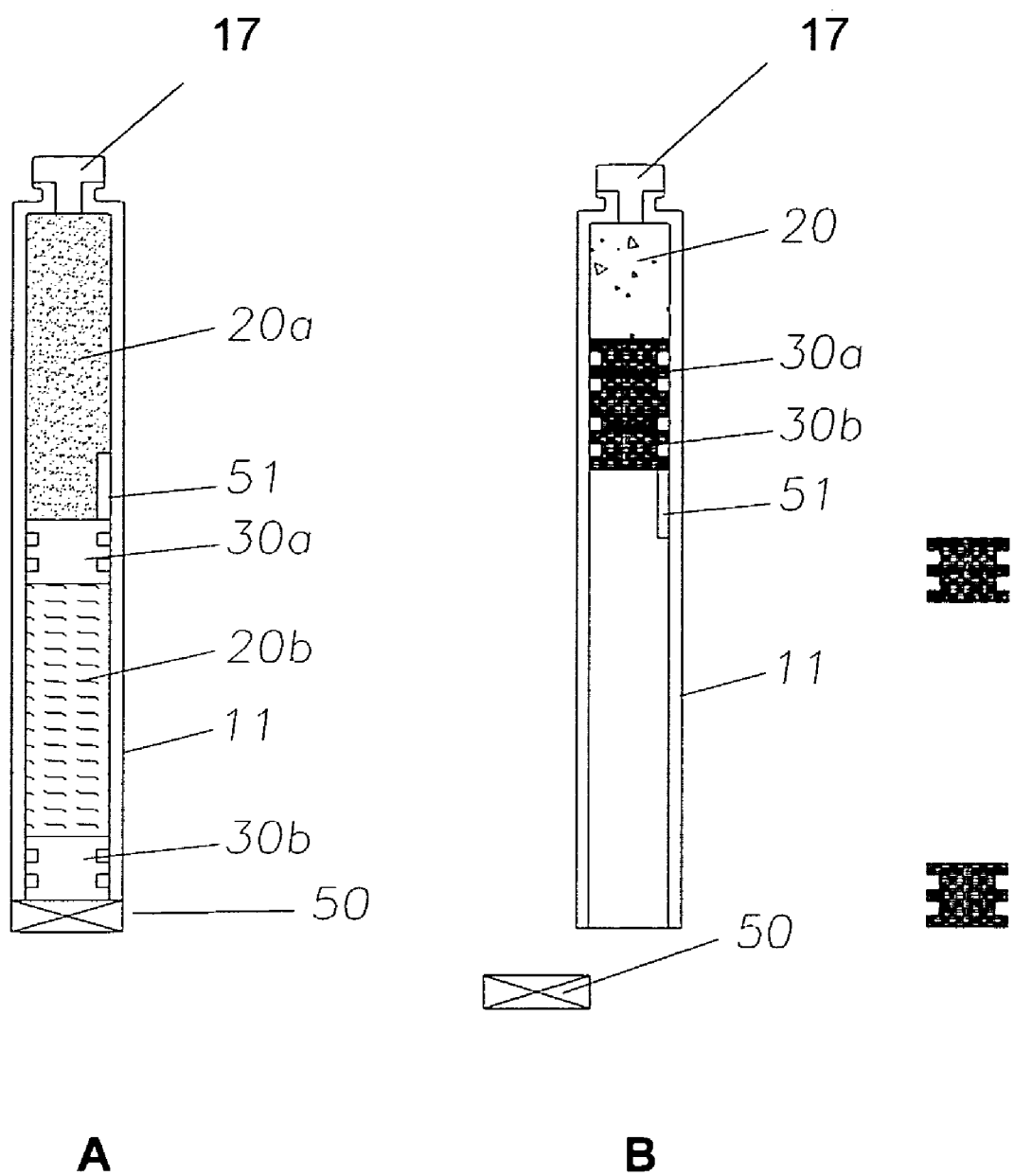
FIG. 17 is a cross-section of a cartridge containing a liquid and a dry drug:
  17A: prior to rehydration;
  17B: after rehydration.
Figure 18:
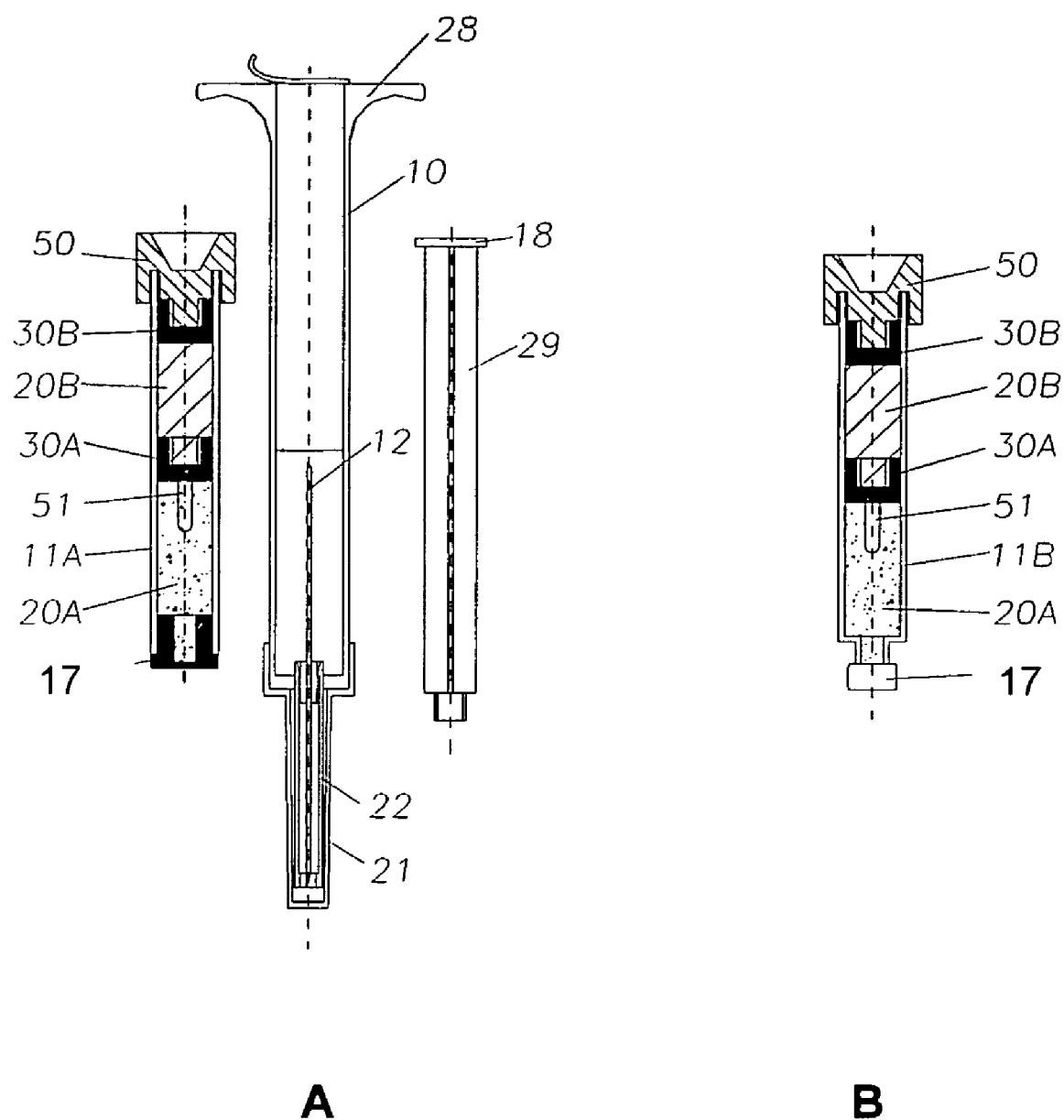
FIG. 18A is a cross-section of the housing with the tube option.
FIG. 18B is a cross-section of the housing with the cartridge option.

FIG. 18 shows device 1 with the tube option 11A or the cartridge option 11B presented with the dual chamber arrangement of FIG. 17. The housing 10 can be the same for both options (11A or 11B). Before removal of releasable lock 50, tube 11A or cartridge 11B cannot be connected on needle 12 through septum cap 17. After removal of releasable lock 50, the rehydration is realized as described in FIG. 17 or FIG. 19 and tube 11A or cartridge 11B can be operably connected to needle 12. The plunger 29 is attached to septum plunger 30B and the injection is performed.

Figure 19:
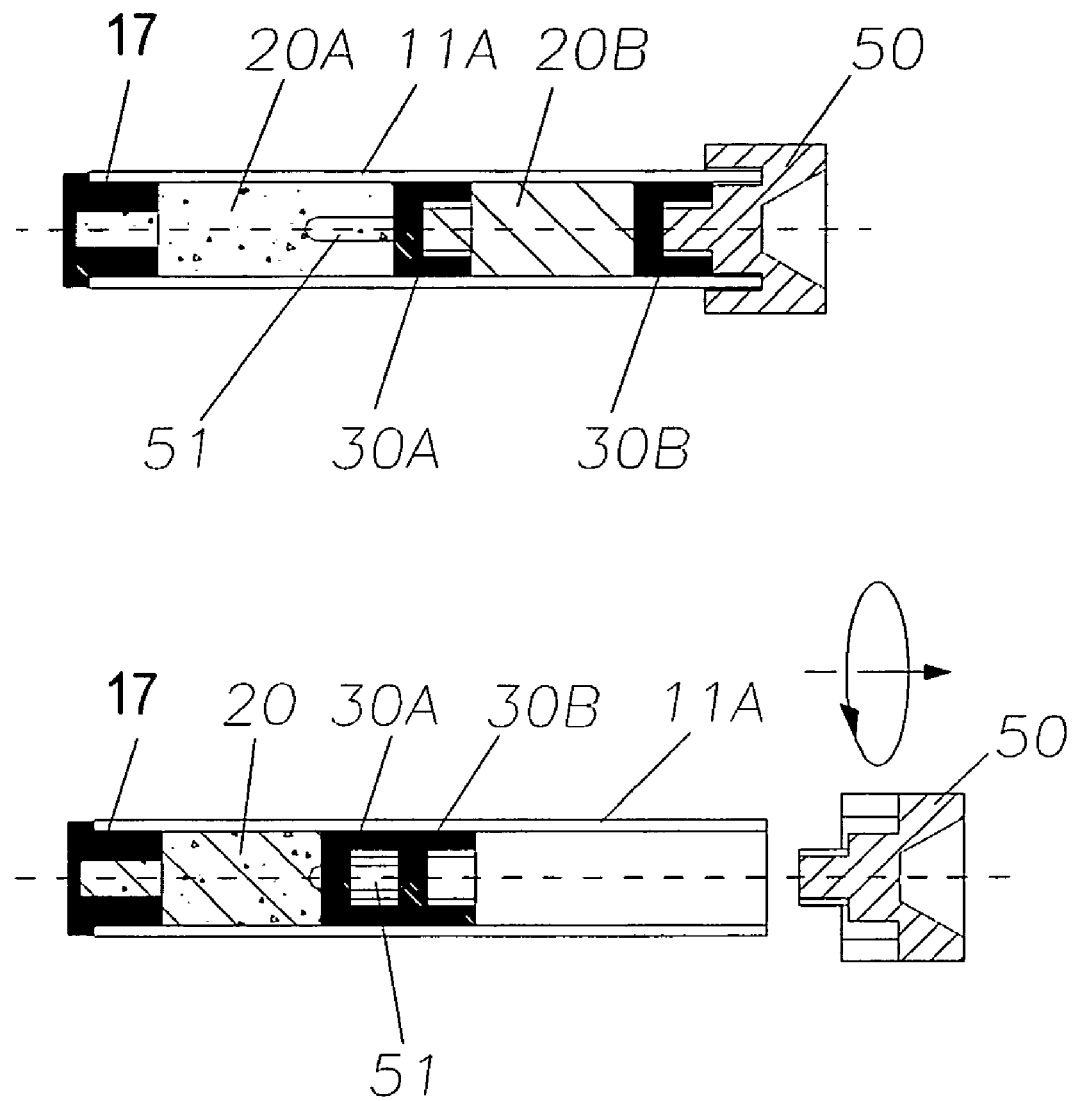
FIG. 19 is a cross-section of the tube containing a liquid and a dry drug before and after rehydration.

FIG. 19 shows, for tube 11A, the rehydration process described in FIG. 17, performed by removing lock 50. Before removing lock 50 on FIG. 12A, tube 11A cannot be introduced into the housing deep enough to introduce needle 12 through septum cap 17 into the tube 11A. Releasable lock 50 also maintains plunger 30A at the top of by-pass 51 despite the vacuum in the solid part of the composition 20A. After removing lock 50 on FIG. 12B, tube 11A can be introduced into the housing to introduce needle 12 through septum cap 17 into the tube 11A. Before this introduction by removing lock 50, the composition 20 is prepared by mixing the solid part 20A and the liquid part 20B due to the rehydration obtained by the vacuum of the chamber containing solid part 20A.

Figure 20:
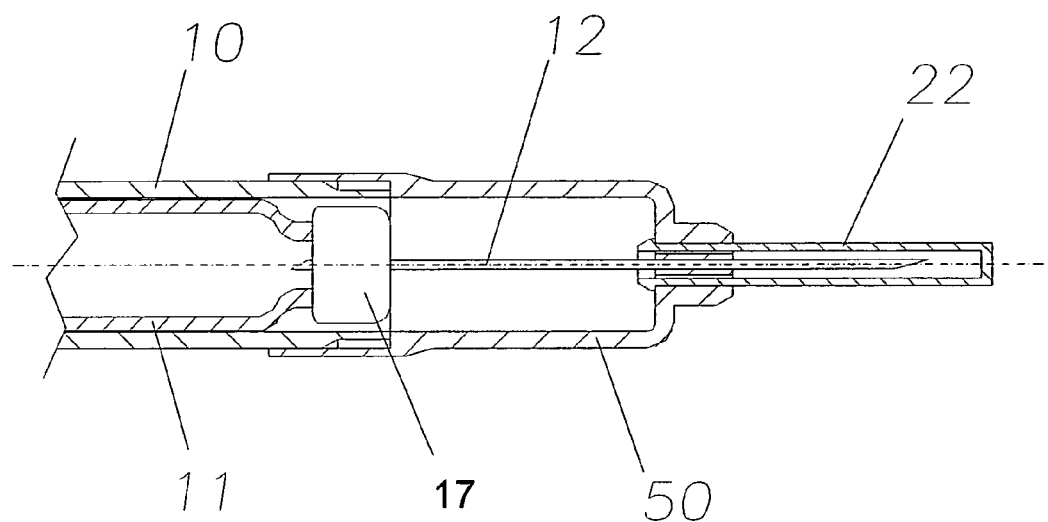
FIG. 20 is a cross-section view at the stage of FIG. 10 in a case where tube containing a liquid and a dry drug before and after rehydration.
Figure 20:
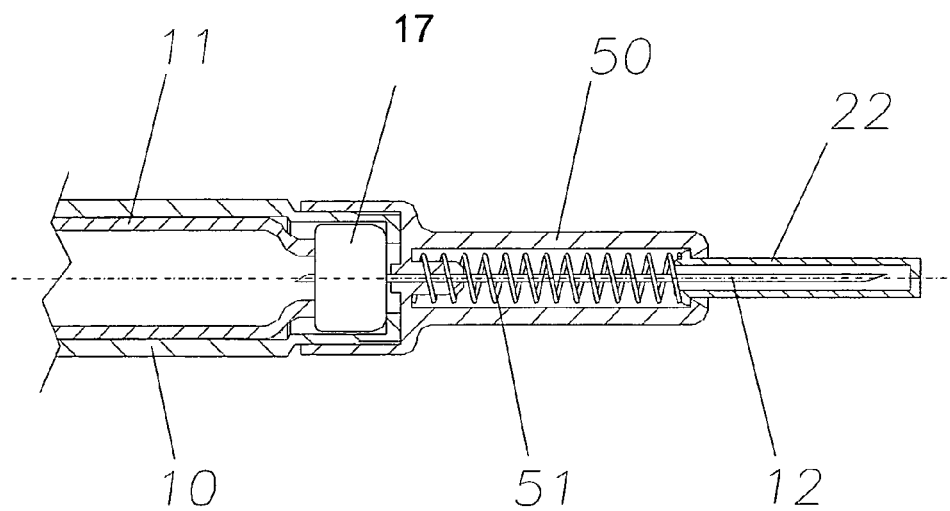

FIG. 20 shows 2 possible variations in the arrangement of FIG. 8 during use after connection of the cartridge or tube 11 on the needle 12 when the needle 12 is not directly attached to the distal end of housing 10 but to a support 50 which corresponds to distal end of housing 10 in the way sleeve 22 is affixed to it.

This independent support 50 can be connected to housing 10, e.g., like a pen or cartridge disposable needle is connected, e.g., by screwing onto housing 10 after needle 12 is introduced through septum cap 17.

In FIG. 20A, the removal of the device from the subject following injection is obtained by sleeve 22 as in FIG. 8 due to the displacement of cartridge or tube 11.

FIG. 20B shows another alternative where the extension of sleeve 22 after injection is facilitated by spring 51 without displacement of cartridge or tube 11. This allows the thread to be a standard one and the device to be adapted on any other existing cartridge pen or syringe injector.

Figure 21:
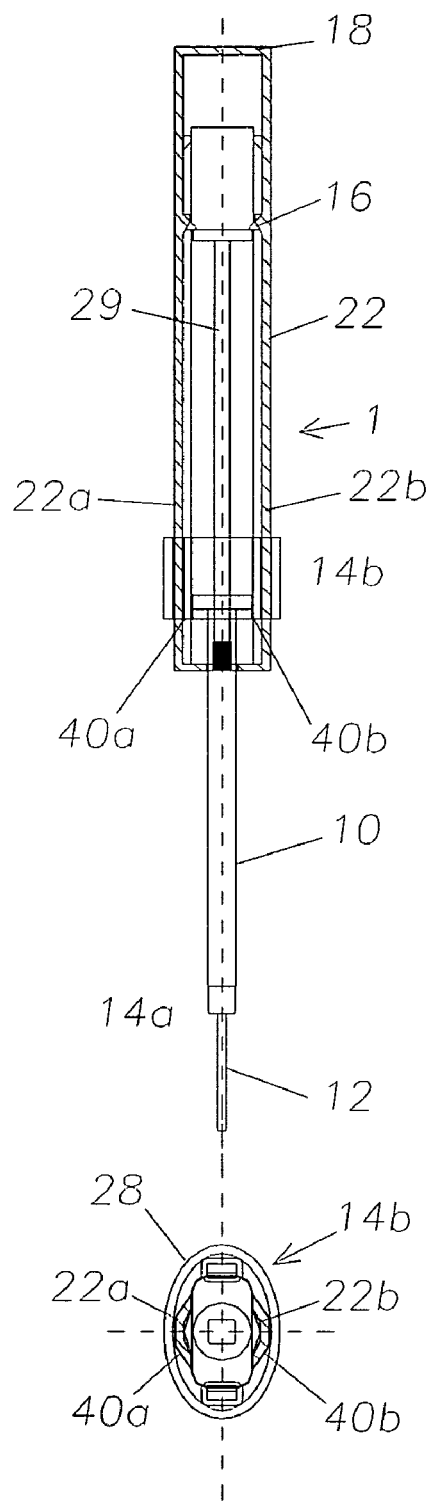
FIG. 21 is a cross-section view of a reservoir injection device prior to use.

FIG. 21 shows injection device 1, including reservoir 10, having a distal end 14a and a proximal end 14b. The proximal end of the reservoir 10 has two holes 40a and 40b adapted to operatively accept arms 22a and 22b. Needle 12 is operatively attached to distal end 14a. Reservoir 10 can be made from a suitably rigid material such as glass, plastic, metal, or the like. The needle 12 is hollow and single-ended outside the reservoir 10 with a tip capable of piercing the skin of a subject. On the proximal end of housing is a flange 28 having, e.g., an elliptic shape, which assists both plunger movement in the reservoir and removal of device 1 from the subject via extension of sleeve 22 following injection.

In this embodiment the sleeve 22 comprises a plunger housing made of a suitably rigid material such as metal, glass, plastic, or the like. The plunger housing 22 surrounds plunger 29 so that when plunger 29 slides into reservoir 10, plunger housing 22 slides around reservoir 10. Plunger housing 22 has longitudinal slots (not shown) and arms 22a and 22b along its length. Arms 22a and 22b pass through holes 40a and 40b respectively in the proximal end 14b.

The proximal end of plunger 29 is covered by plunger housing 22 up to a flange 18. Flange 18 assists depression of plunger 29 into reservoir 10 along with simultaneous depression of plunger housing 22 around reservoir 10 due to the removable lock 17 or connection means with plunger 29 into plunger housing 22.

Figure 22:
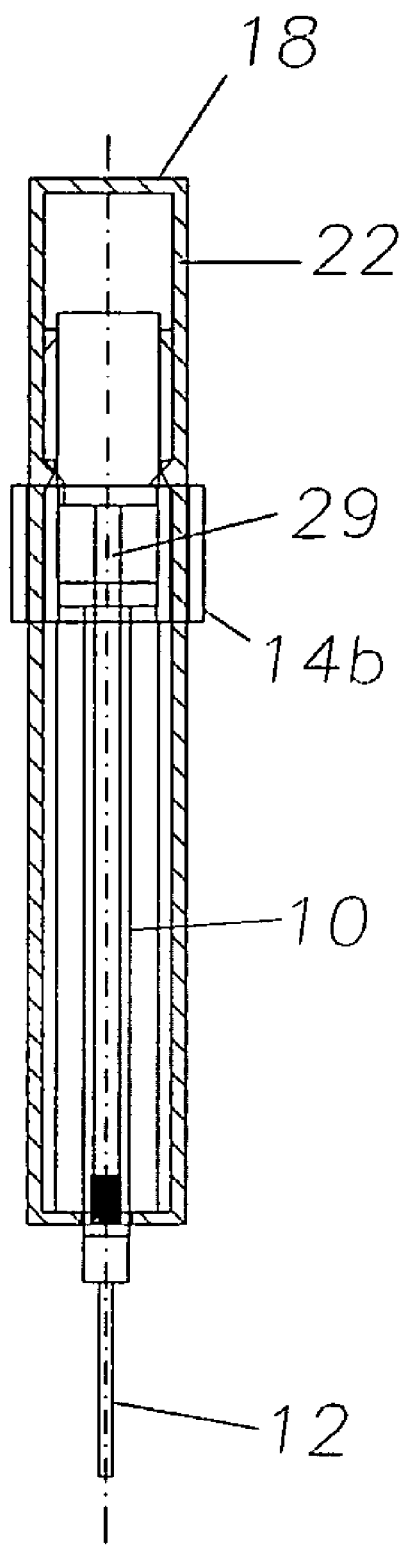
FIG. 22 is a cross-sectional view of the reservoir injection device after drug composition injection.

FIG. 22 shows device 1 as depicted in FIG. 21 wherein plunger 29 has been depressed by plunger housing 22 thereby injecting composition from reservoir 10 through needle 12.

Once composition has been injected plunger 29 rests against the bottom or distal end of reservoir 10, which is also completely covered by plunger housing 22.

Reservoir 10 is then moved away from the injection needle site by exerting pressure against the lower part of the flange on proximal end 14b of the reservoir 10 while simultaneously exerting opposing pressure on flange 18 of plunger housing 22. This relative movement of the plunger housing 22 and reservoir 10 causes plunger 29 to be released from removable lock 16 due to sliding guide and release mechanism on reservoir proximal end 14b, and plunger housing slides around reservoir 10 and needle 12, which in turn urges needle 12 out of injection site.

Figure 23:
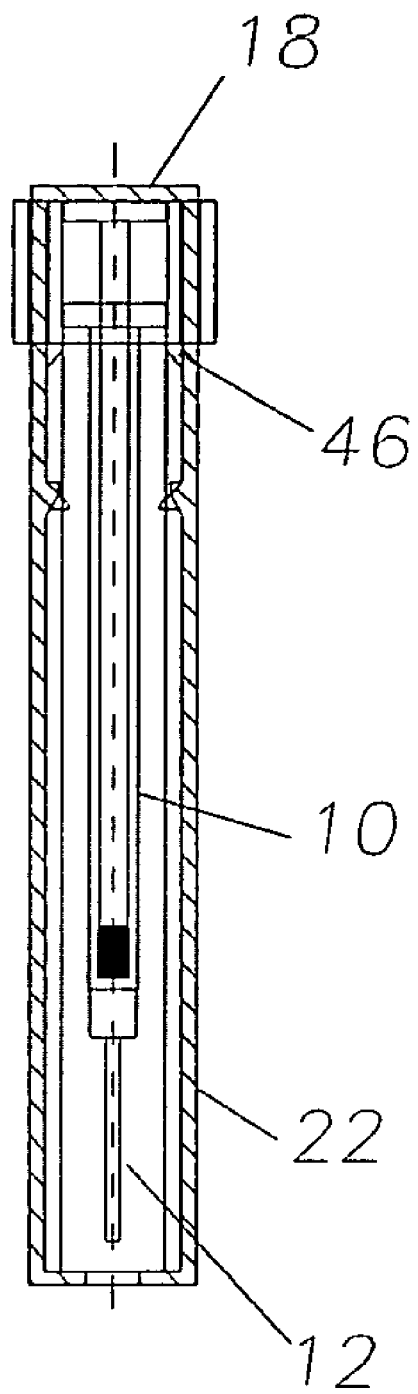
FIG. 23 is a cross-sectional view of the reservoir injection device following complete withdrawal of the needle from the subject.

FIG. 23 shows needle 12 fully withdrawn from the injection site and plunger housing 22 covering reservoir 10 and needle 12.

Flange 18 is equipped with means 46 to secure, optionally irreversibly, the plunger housing 22 once the needle 12 has been protected.

Composition 20 is a liquid or a semi-solid composition containing a drug. The drug of composition 20 can be any drug capable of being parenterally administered as a liquid or a semi-solid. For example, the drug can be a vaccine, a peptide, a protein, or a small chemical entity. Examples of suitable drugs include, e.g., insulin and heparin. For drugs which are not stable in liquids over an extended period of time, the liquid and the dry drug can be stored in separate chambers within housing 10. The device can be configured such that the liquid and the dry drug are combined together just prior to injection.

For example, the chamber created between septum plunger 16 and plunger tip 30 (e.g. in FIG. 1) in housing 10 can be separated into two separate parts by a fixed wall or film that can be punctured, e.g. by pressure of the plunger 29 on the plunger tip 30, or a puncturing means. Alternatively, the two parts of the chamber can be separated by a moving wall or septum. In this case, the top or proximal part of the chamber above the moving wall or septum contains the liquid portion of the composition, and the distal part of the chamber contains the solid, e.g., powder, portion of the composition. When plunger 29 is urged into housing 10, it applies pressure to plunger tip 30 and plunger tip 30 applies pressure to the liquid portion of the composition. This, in turn, applies pressure on the moving septum, causing it to move in a distal direction. The housing is configured with a liquid bypass (e.g., a bulge or passage in the housing wall) in a location that initially prevents passage of liquid from one part of the chamber to the other, but when the moving septum reaches a specific location, the bypass allows the liquid to pass from the top or proximal part of the chamber into the lower or distal part of the chamber on the other side of the moving septum.

To maintain sterility, the device of the invention can be stored in a conventional blister pack or pouch prior to use.

Other Embodiments

It is to be understood that while the invention has been described in conjunction with the detailed description thereof, the foregoing description is intended to illustrate and not limit the scope of the appended claims. Other aspects, advantages, and modifications are within the claims.

What is claimed is:

1. An injection device for injecting a composition into a subject, the device comprising:
 a hollow housing (10) having a proximal end and a distal end, said distal end being configured to contain a liquid (20B) and a solid drug composition (20A) separate from each other, wherein said liquid (20B) and said solid drug composition (20A) are combined in said housing (10) prior to injection to form a composition (20) for injection into a subject;
 a hollow needle (12) affixed to the distal end of the housing (10), said needle (12) having a distal end extending outside of the housing (10) and having a proximal end extending longitudinally within said housing (10);
 a plunger (29) comprising a proximal end and a distal end, said plunger (29) arranged to slide within the proximal end of the housing (10);
 a septum plunger (16) slidably arranged within the housing (10) between the plunger (29) and the distal end of the housing (10), said septum plunger (16) being configured to isolate the composition (20) between the septum plunger (16) and the distal end of the plunger (29);
 a hollow sleeve (22) slidably connected to the distal end of the housing (10) and arranged to cover the needle (12) prior to injection, to retract into the housing (10) during injection and to cover the needle (12) after the injection upon contact with said septum plunger (16) as said septum plunger (16) is displaced by said plunger (29) towards the distal end (14b) of said housing (10); and
 wherein the device (1) is designed such that when the sleeve (22) is pressed against the subject (34), the sleeve (22) retracts into the housing (10) thereby allowing the needle (12) to penetrate into the subject (34), and when the plunger (29) is pushed into the housing (10), the proximal end of the needle (12) pierces the septum plunger (16) thereby exposing the proximal end of the needle (12) to the previously isolated composition (20) and the composition (20) is pushed from the housing (10) into and through the needle (12) and into the subject (34).

2. The device (1) of claim 1, wherein the proximal end (14a) of the housing (10) comprises a flange (28).

3. The device (1) of claim 1, wherein the proximal end of the plunger (29) comprises a flange (18).

4. The injection device (1) of claim 1, wherein the device (1) is further configured such that when the composition (20) is pushed out of the housing (10), the plunger (16) moves the sleeve (22) out of the housing (10) to cover the needle (12).

5. The device (1) of claim 4, wherein the housing (10) contains the liquid or semi-solid composition (20).

6. The device (1) of claim 1, wherein the housing (10) contains the liquid or semi-solid composition (20).

7. The device (1) of claim 1, wherein the device (1) further comprises a releasable lock (25) to prevent the plunger (29) from sliding in the proximal end of said housing (10).

8. The device (1) of claim 1 which further comprises a removable cap (21) which covers the sleeve (22).

9. The device (1) of claim 1, wherein said septum plunger (16) contains a bore (26) which the needle (12) pierces the septum plunger (16) at bore (26) during use of said injection device (1).

* * * * *